(12) United States Patent
Roques et al.

(10) Patent No.: US 6,813,020 B2
(45) Date of Patent: Nov. 2, 2004

(54) DEVICE FOR DETERMINING THE VALUES OF AT LEAST ONE PARAMETER OF PARTICLES, ESPECIALLY OF WATER DROPLETS

(75) Inventors: Sandrine Roques, Rebigue (FR); Christian Lopez, Le Castera (FR)

(73) Assignee: Airbus France, Toulouse (FR)

( * ) Notice: Subject to any disclaimer, the term of this patent is extended or adjusted under 35 U.S.C. 154(b) by 399 days.

(21) Appl. No.: 09/979,886

(22) PCT Filed: Mar. 21, 2001

(86) PCT No.: PCT/FR01/00842

§ 371 (c)(1),
(2), (4) Date: Nov. 27, 2001

(87) PCT Pub. No.: WO01/77644

PCT Pub. Date: Oct. 18, 2001

(65) Prior Publication Data

US 2002/159060 A1 Oct. 31, 2002

(30) Foreign Application Priority Data

Apr. 7, 2000 (FR) .............................. 00 04432

(51) Int. Cl.[7] .............................................. B01N 15/02
(52) U.S. Cl. ........................ 356/336; 356/338; 356/343
(58) Field of Search ................................ 356/335–343; 340/962, 580, 581, 583, 584, 600–602; 250/574, 573, 575

(56) References Cited

U.S. PATENT DOCUMENTS 4,975,237 A * 12/1990 Watling ...................... 356/338
5,455,675 A * 10/1995 Witt et al. ................... 356/336
5,484,121 A   1/1996 Padawer et al.
5,610,712 A * 3/1997 Schmitz et al. .............. 356/335
6,075,591 A * 6/2000 Vokhmin .................. 356/239.1
6,091,335 A * 7/2000 Breda et al. ................. 340/580

FOREIGN PATENT DOCUMENTS

| DE | 19510034 | 9/1996 |
| EP | 0405625 A2 | 1/1991 |
| FR | 2689247 A1 | 10/1993 |
| GB | 2158939 A | 11/1985 |
| WO | 9429762 | 12/1994 |
| WO | 9512118 | 5/1995 |

* cited by examiner

*Primary Examiner*—Frank G. Font
*Assistant Examiner*—Layla Lauchman
(74) *Attorney, Agent, or Firm*—Stevens, Davis, Miller & Mosher, LLP.

(57) ABSTRACT

A device for determining the values of a parameter of particles, especially of water droplets, includes a measuring element having a measuring region that is intended to accommodate the particles. An illumination device illuminates the measuring region with a light beam, and an image acquisition device, having a camera, acquires an image of the measuring region illuminated by the illumination device. A processing device determines the values of the parameter from the image acquired by the camera. To determine the values of the parameter, the illumination device produces point illumination using a light beam whose light rays are focused on an objective optic of the image acquisition devices.

19 Claims, 4 Drawing Sheets

DEVICE FOR DETERMINING THE VALUES OF AT LEAST ONE PARAMETER OF PARTICLES, ESPECIALLY OF WATER DROPLETS

The present invention relates to a device for determining the values of at least one parameter, especially the size, of particles such as water droplets.

Although not exclusively, said device is applicable more particularly to the detection and to the characterization of icing conditions on aircraft, especially civil transport airplanes, by making it possible to measure the size and the number of water droplets present in particular in the clouds and the fogs through which an aircraft passes.

It is known that the problem of rapid formation of ice on an aircraft is a serious problem which may lead to accidents when it occurs suddenly and when it could not be detected in time.

By means of documents U.S. Pat. No. 5,484,121, EP-0 405 625 and GB-2 158 939, devices are known for detecting the presence of ice on the external parts of an aircraft, especially the wings, once this ice is formed. These devices use, to this end, light beams and involve the reflection of these light beams in order to detect the presence of ice. If necessary, a signal is emitted in order to inform the pilot that it is necessary to activate a deicing device.

These known devices especially have the drawback of warning the pilot only when the ice is already formed. Therefore they do not allow the phenomenon of ice formation to be anticipated so that decisions suited to the climatic conditions can be taken before a problem appears.

Other devices are known for characterizing icing conditions, especially during development or test flights. It is known that, during development flights, it must be demonstrated that the conditions encountered comply properly with the regulatory requirements decreed by the certification authorities, which then validates the behavior of the airplane under such conditions.

The known devices, used to this end, are generally intended to determine the particle size distribution of clouds, that is to say the size, the number and the shape of the water droplets present in these clouds, and they can be classified in two categories:
particle counters which determine the characteristics of each particle, taken individually; and
integrators which sum the contributions from all the particles present in a measuring volume.

These known devices may also be classified according to their measurement principle, namely in particular:
imaging or shadowgraphy,
the Doppler effect, or
light scattering (measurement along given angles).

By way of illustration, it is possible to mention some examples of known devices implementing imaging and shadowgraphy principles and acting, for example, as particle counters.

Firstly, a device which is known by the term "Optical Array Probe" implements, in a standard manner, the principle called linear array shadowgraphy. In this case, a particle passing through a collimated light beam produces a shadow directly related to its diameter on a linear array of detectors spaced apart at equal intervals. When there is no particle in the measuring volume in question, the light beam illuminates all the detectors. On the other hand, when a particle passes through said measuring volume, a loss of light due to scattering, refraction and absorption of the particle generates a signal at the output of the detectors. The number of detectors showing a variation in amplitude of more than a specific threshold (for example 50%) is summed in order that the size of the particle is given directly. However, this known device has a limited measurement range and is not able to measure particles accurately, if their diameter is less than 100 $\mu$m.

Secondly, a device which is known by the term "Cloud Particle Imager" generates two laser beams. The intersection of these two lasers beams defines a rectangular sampling area. Any particle which passes through this rectangular sampling area is properly focused and actuates illumination by an imaging laser, for the purpose of acquiring an image. Detectors are placed facing the laser beams: they make it possible to detect the passage of particles by measuring the decrease in intensity produced as these particles pass through. The diameter of the particles is measured from the image of the properly focused particle. However, this known device is bulky and has too large a volume to improve the operational difficulties stated above and linked to the devices currently used in in-flight testing.

Thirdly, a measuring device is known by document FR-2 689 247, in particular comprising:
a rod comprising a measuring region which is intended to accommodate the particles to be analyzed;
illumination means capable of illuminating said measuring region, using at least one laser beam;
image acquisition means capable of acquiring images of said measuring region illuminated by said illumination means; and
processing means capable of determining the values of said parameter, from said images.

More specifically, the latter known device emits a pulsed light beam that is transported by optical fiber and which is focused onto the measuring region. The image is also transported by optical fiber up to a beam splitter which divides and orients the beam toward the image acquisition means comprising two "CCD"-type sensors. A first image is recorded along a particular sighting axis on one of the sensors. After a very short time, a second image is recorded along the same sighting axis on the other sensor. On subtracting these two images, a dark/light doublet is obtained which stands out well against the uniform background, from which it is possible to deduce the size and the velocity of the imaged particles. This known device makes it possible to remove the majority of background defects. This is because the image acquisition means with a double sensor behave like a double shutter and only see the field for two very short periods of time.

However, this known device has a small measuring volume. It is known that the measuring volume analyzed per second is equal to the measuring volume associated with each image, multiplied by the image rate of the image acquisition means.

As to the measuring volume associated with each image, this is related to the size of the sensor (divided by the magnification) and to the depth of field.

Consequently, in particular because of its small measuring volume, the known device disclosed by document FR-2 689 247 is not suitable for the applications envisaged in the present invention, relating to the measurement of water droplet parameters since, especially because of the often relatively low concentrations of water droplets present in the clouds analyzed during tests, a large measuring volume is needed for such an application.

It will be noted, moreover, that the various known devices comprise various drawbacks which are problematic for the aforementioned preferred application. This is because the known devices are, in general, poorly adapted to the envisaged meteorological and operational constraints, in particular because of the following difficulties, namely a long and difficult installation in an aircraft, a very large bulk, difficult exploitation of the results, etc. Furthermore, the majority of these known devices have a range for measuring of the size of the droplets which is small, and especially are not able to detect and analyze, at the same time, the small droplets and the large supercooled droplets (water at a temperature less than 0° C.) which, as is known, promote the appearance of ice.

The present invention relates to a device for determining the values of at least one parameter, especially the size, of particles, in particular of water droplets, which makes it possible to overcome the aforementioned drawbacks and which especially comprises an increased measuring volume.

To this end, according to the invention, said device of the type comprising:

a measuring element comprising a measuring region which is intended to accommodate the particles;

illumination means capable of illuminating said measuring region;

image acquisition means comprising at least one camera capable of acquiring at least one image of said measuring region illuminated by said illumination means; and processing means capable of determining the values of said parameter, from said image acquired by the camera, is noteworthy in that said illumination means are constituted so as to produce a point illumination source using a light beam, the light rays of which are focused on an objective optic of the image acquisition means.

Thus, by means of this point illumination, the contrast (on the image or images acquired) of the shadow of the particles located in the measuring region is increased. This increase in contrast leads to an improved observability of the particles at the expense of focus and therefore an increase in the depth of field, since the image remains observable for higher defocused values. This increase in depth of field itself leads to an increase in the measuring volume which, as indicated above, depends on the size of the sensor and on the depth of field.

In a preferred embodiment, in order to produce said point illumination, said illumination means comprise at least one optical assembly comprising:

a light source, preferably a laser source, capable of generating a light beam;

an optical fiber connected by a first end to said light source and capable of transmitting a light beam generated by the latter; and a field optic fitted to a second end opposite said first end of said optical fiber and focusing the light beam emerging from said optical fiber onto the center of the objective optic of the camera of said image acquisition means.

Preferably, said optical fiber is a monomode fiber, that is to say a fiber which, by construction, makes it possible to transmit only a single mode of a laser beam. This makes it possible to prevent the appearance of unwanted noise.

Furthermore, in order to yet further increase the measuring volume, in an advantageous manner:

said illumination means comprise a light source generating a coherent light beam, which makes it possible to increase the aforementioned contrast; and/or a camera is used which has a high image acquisition rate; and/or said camera comprises means which open the latter in order to acquire an image, said illumination means produce illumination in the form of light flashes, and are controlled so as to emit at least two light flashes during one and the same opening of the camera on acquiring an image. Thus, the measuring volume which is observed during the camera opening period is increased.

In order to implement the last characteristic, preferably, said illumination means comprise a pulsed laser with a saturable absorber in order to emit said light flashes, that is to say a laser making it possible to emit light flashes of very short durations. This makes it possible to compensate for the flow velocity of the particles. In effect, the light flash freezes the particles.

Moreover, in order to increase the size range of measured particles, especially of water droplets, in an advantageous manner, said illumination means are constituted so as to emit in a sequential manner at least two light beams dedicated to measuring different diameters.

In order to do this, in a preferred embodiment, said illumination means comprise two laser sources associated with optics of different magnifications respectively, and said image acquisition means comprise a single camera and optical means making it possible to direct the two laser beams emitted by said two laser sources, onto said camera.

In order to yet further increase the measurement range, said processing means are constituted so as to determine said parameter by shadowgraphy.

Moreover, advantageously, said illumination means are constituted so as to emit two light flashes spaced apart by a predetermined duration, said camera is constituted so as to acquire an image on emission of each of said light flashes, and said processing means are constituted so as to determine, as a parameter, the velocity vector of said particles, from the superposition of two images relating to said two light flashes and from said predetermined duration.

To this end, said illumination means preferably comprise a light source and an optical fiber which is connected to said light source.

In addition, advantageously, the device according to the invention further comprises:

an interference filter which is fitted to the entrance of said camera, in order to filter out the unwanted light which might reach the camera; and/or an antireflection treatment in order to prevent interference; and/or a measuring region which is delimited by at least one window; and/or means to blow air, preferably filtered air, over the external face of said window, which prevents the appearance of dirt on said window.

In a preferred embodiment, said measuring element is a rod provided with a through opening, preferably oblong, at a first of its ends, said through opening containing said measuring region.

In addition, advantageously, the device according to the invention also comprises a protection specified below, which protects the entire said device, except for at least said first end of the rod which is itself placed directly into the environment containing said particles, against said particles which are generally moving.

In addition, advantageously, at least said first end of the rod is electrically insulated so as to make the device according to the invention unattractive to lightning, for example, if said device is fitted onto an aircraft, as specified below.

Moreover, it will be noted that the device according to the invention is particularly well suited to provide certification authorities with reliable quality information on the conditions encountered by an aircraft during in-flight tests. Of course, there may be other possibilities of use thereof, such as the certification of helicopters during stationary flights, the verification of conditions produced in icing wind tunnels, measurements on the ground during poor conditions of visibility (fog, etc.), etc.

Another beneficial application relates to the prevention and anticipation of icing conditions on an aircraft. Specifically, as indicated above, the majority of existing devices only warn the pilot once the ice is established on the sensitive regions of the aircraft. In contrast, the understanding of the conditions which lead to the formation of ice by studying droplets which form the cloud, combined with temperature information, makes it possible to anticipate this ice formation. Thus, by means of a device according to the invention which makes it possible to study water droplets over the whole measurement range involved, it is possible to warn the pilot of the probable formation of ice before the latter is formed on the sensitive regions of the aircraft.

The present invention also relates to an aircraft, in particular a civil transport airplane, which is noteworthy in that it comprises a device as mentioned above, for determining the values of said parameter of water droplets present outside said aircraft.

Advantageously, said aircraft further comprises a sleeve:
which is fitted into the fuselage of the aircraft so as to create a through opening;
which has a diameter adapted to the diameter of the aforementioned rod of the device according to the invention such that the latter can be fitted in a sealed manner in said sleeve; and
which is capable of being closed in a sealed manner, in the absence of said rod.

Thus the device according to the invention can be mounted and dismantled easily and quickly. In addition, the aerodynamics of the aircraft are only slightly altered.

The figures of the appended drawing will make it easy to understand how the invention may be produced. In these figures, identical references denote similar elements.

The device 1 according to the invention is intended to determine at least one parameter, such as the size, the velocity or the direction of movement of particles such as water droplets, for example.

Figure 3:
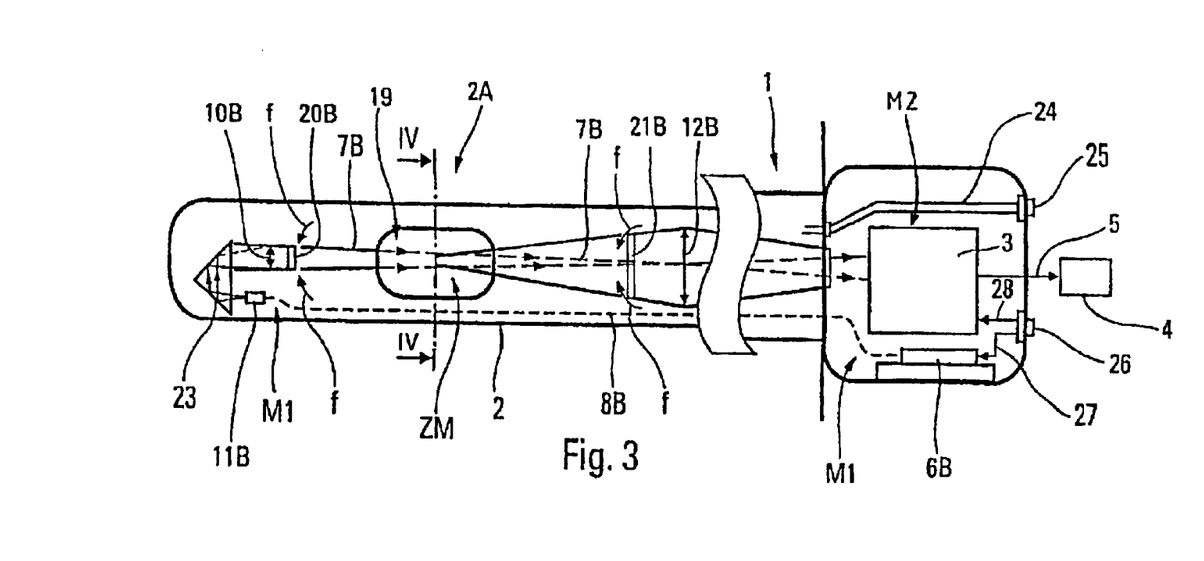
FIGS. 3 and 5 are schematic lateral and bottom views, respectively, of a preferred embodiment of the device according to the invention.
Figure 4:
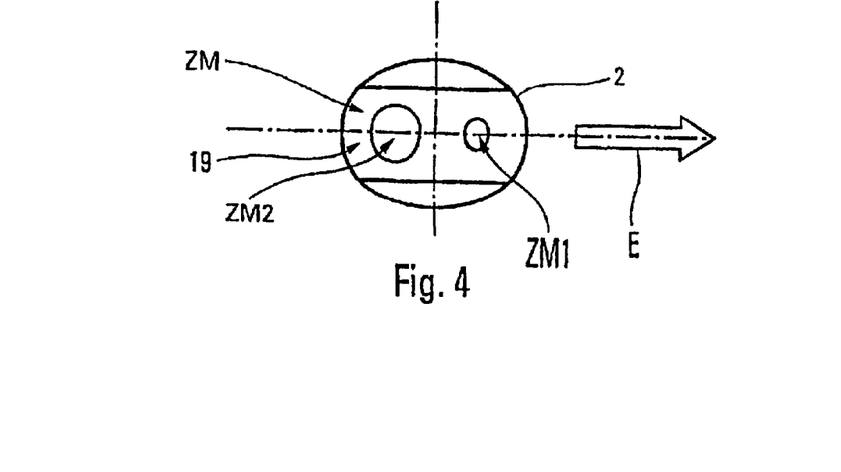
FIG. 4 is a schematic section along line IV—IV of FIG. 3.
Figure 5:
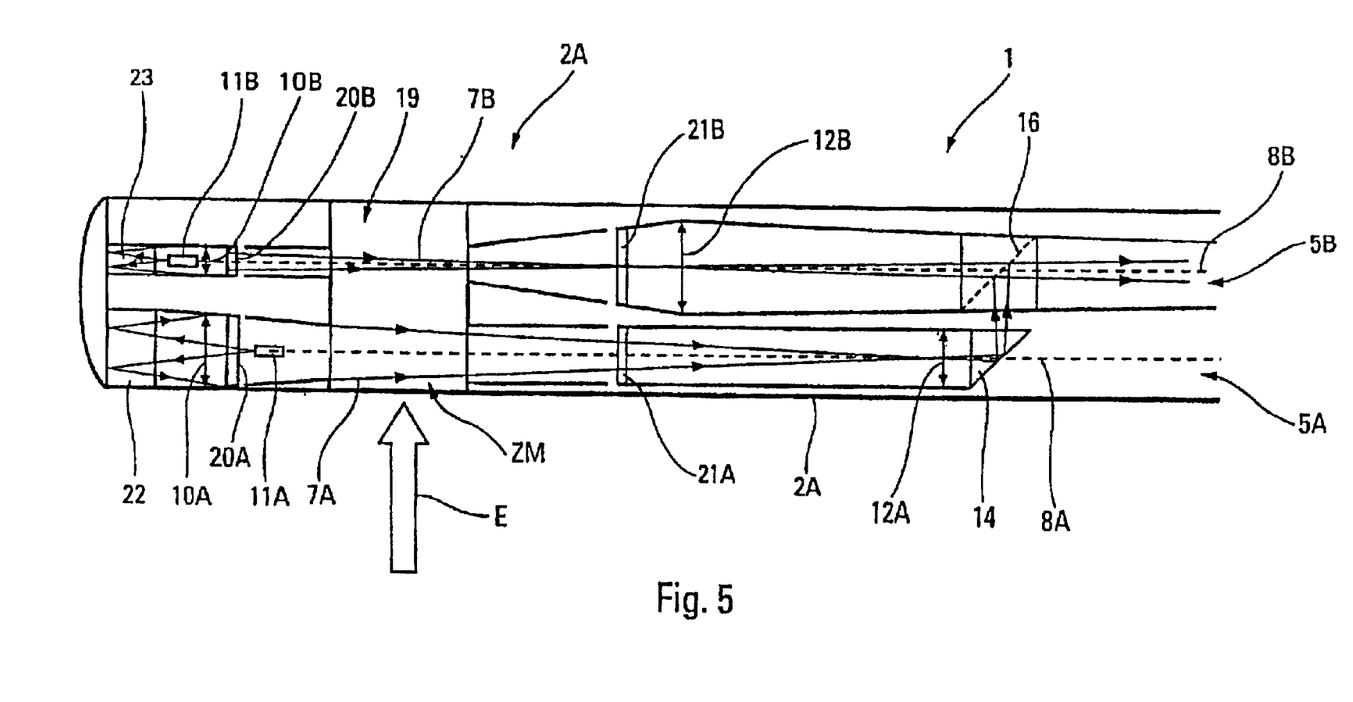

To this end, said device 1 comprises, in a known and general manner, as shown in a preferred embodiment in FIGS. 3 to 5:

a measuring element 2 comprising a measuring region ZM which is intended to accommodate said particles;

illumination means M1 specified above capable of illuminating said measuring region ZM, using at least one light beam 7A, 7B;

image acquisition means M2 comprising at least one camera 3 capable of acquiring at least one image of said measuring region ZM illuminated by said illumination means M1; and a processing unit 4 connected to said image acquisition means M2 via a connection 5 and capable of determining, preferably by shadowgraphy, the values of said parameter, from said image acquired by the camera 3.

According to the invention, said illumination means M1 are constituted so as to produce point illumination, using a light beam 7A, 7B comprising light rays RA, RB which are focused in the manner indicated above.

Figure 1:
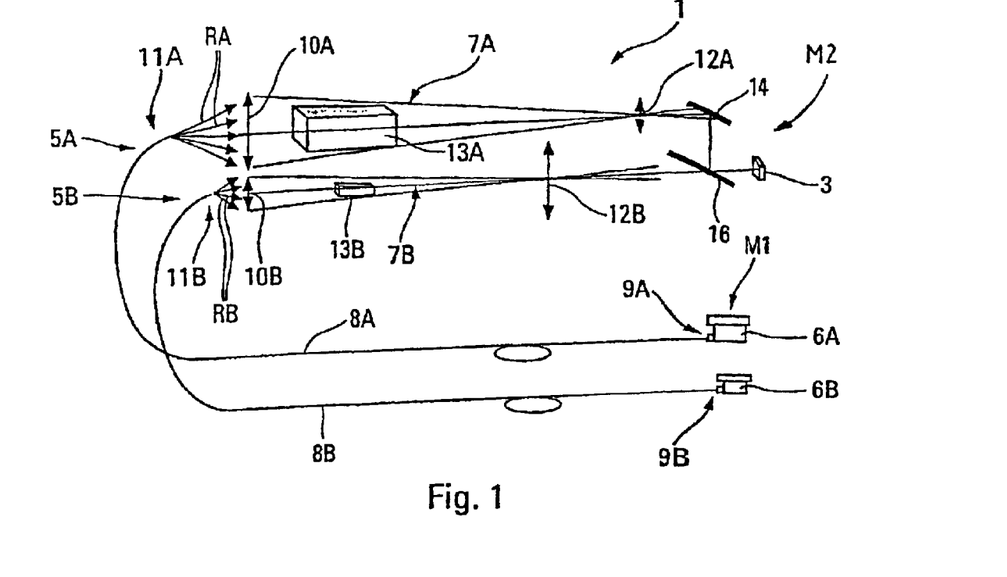
FIG. 1 illustrates schematically a device according to the invention.

To this end, in a preferred embodiment, said illumination means M1 comprise, as shown schematically in FIG. 1, at least one optical assembly 5A, 5B comprising:

a light source 6A, 6B, preferably a laser source, capable of generating a light beam 7A, 7B;

an optical fiber 8A, 8B connected by a first end 9A, 9B to said light source 6A, 6B and capable of transmitting a light beam 7A, 7B generated by the latter; and a field optic 10A, 10B fitted to a second end 11A, 11B opposite said first end 9A, 9B of said optical fiber 8A, 8B and focusing the light beam 7A, 7B emerging from said optical fiber 8A, 8B onto an objective optic 12A, 12B of the camera 3 of said image acquisition means M2.

The field optic 10A, 10B focuses the light beam 7A, 7B emerging from the optical fiber 8A, 8B, preferably a laser beam, at the center of the objective optic 12A, 12B, that is to say channels the rays RA, RB of said emerging light beam 7A, 7B.

Figure 2:
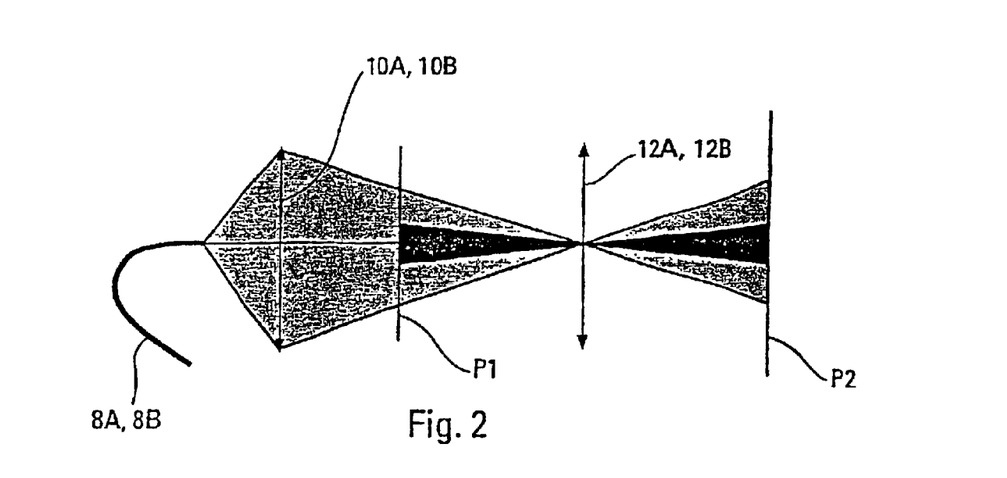
FIG. 2 is an optical diagram making it possible to illustrate the principle of operation of the device according to the invention.

The objective optic 12A, 12B forms the image of the object in the conjugate plane. In order to better demonstrate this characteristic, the object plane P1 and the plane P2 of the camera 3 are shown in FIG. 2.

By means of this "point" illumination, the contrast (on the image or images acquired) of the shadow of the particles located in the measuring region ZM (plane P1) is increased. This increase in contrast leads to improved observability of the particles at the expense of focus and therefore an increase in the depth of field, since the image remains observable for higher defocused values. This increase in the depth of field itself leads to an increase in the measuring volume which depends in a known manner both on the size of the sensor, preferably a CCD sensor, on the camera 3 and on the depth of field.

It will be noted that with standard shadowgraphy by illumination which is hot point illumination (i.e. diffuse illumination) as disclosed, for example, by the aforementioned document FR-2 689 247, the shadows produced by each point of the light source do not exactly overlap. The shadow of the object is therefore illuminated by the unwanted light coming from said source, which, of course, is detrimental to the contrast. This problem is efficiently remedied by virtue of the present invention.

According to the invention, the optical fiber 8A, 8B is a monomode fiber. By construction, this type of fiber makes it possible to transmit only one mode of the laser beam 7A, 7B and therefore prevents any unwanted noise. The surface of the "source" is therefore reduced to a diameter of a few microns. In addition, the use of an optical fiber makes it possible for the light source 6A, 6B to be easily fitted in a protected region, for example in the cabin of an airplane.

Furthermore, according to the invention, the field optic 10A, 10B and the objective optic 12A, 12B may be single lenses or sets of lenses.

In addition, the diameter of the objective optic 12A, 12B is dimensioned so that the accuracy of measurements is not degraded by diffraction phenomena. These phenomena are related to the size of the entrance pupil (diameter of the objective optic) and to the wavelength used. Thus, in order to avoid such diffraction problems, a laser source of the doubled "YAG" type at a preferred wavelength of 532 nm is used.

Furthermore, in order to yet further increase the measuring volume, especially thereby contributing to an increase in contrast, in an advantageous manner:

said illumination means M1 comprise at least one light source 6A, 6B, preferably a laser source, generating a coherent light beam 7A, 7B, which makes it possible to increase the aforementioned contrast;

a camera 3 is used which has a high image acquisition rate, for example a camera of the "CAD6" type, enabling a rate of 262 frames/second with a resolution of 512=512 pixels to be achieved; and in a particular embodiment, said camera 3 comprises known means (not shown), which open the latter in order to acquire an image, said illumination means M1 produce illumination in the form of light flashes and are controlled so as to emit at least two light flashes during an opening of the camera 3 on acquiring an image. Thus the measuring volume observed during the opening period of the camera 3 is increased.

This is only possible by decreasing the intensity of the laser beam so as not to saturate the camera 3. In practice, it is preferred to limit the number of light flashes to two or three, since this technique has the drawback of decreasing the signal/noise ratio. Thus the volume observed during the opening period of the camera is multiplied by the number of light flashes provided per image.

It will be noted that the periodicity of these light flashes takes account of the dump time of the pixels from the camera 3 (dead time during which the acquisition of a new image is not possible).

In addition, the use of short-duration light flashes makes it possible to compensate for the flow velocity of the particles. In effect, such a light flash freezes the particle. The device 1 according to the invention therefore makes it possible to measure the characteristics of particles such as water droplets, for almost zero velocities up to high velocities (V>150 m/s). Nevertheless, for high velocities, it is necessary to illuminate the droplets with light flashes with a short enough duration to freeze them in their movement. For air velocities of around 100 to 150 m/s, the duration of the flash must not exceed 5 to 10 ns. It is for this reason that the preferred laser source is a pulsed laser with a saturable absorber (of the "Q-switch"type) which generates pulses of duration less than 1 ns. In addition, this laser source has the advantage of being lightweight and of low bulk.

Moreover, in order to increase the range of measurement of the size of particles or water droplets, the illumination means M1 comprise, according to the invention, as shown in FIGS. 1 and 5, the two aforementioned optical assemblies 5A and 5B, each emitting in a sequential manner a laser beam 7A and 7B of different diameter adapted to the field observed. This difference in diameter, which is due in particular to different magnifications of the optics 12A, 12B, is illustrated in FIG. 1 by rectangular parallelepipeds 13A and 13B of different sizes.

By way of illustration, the optics 12B and 12A can be adjusted in order to procure, respectively, a magnification of 3, adapted to observing small droplets (from about 10 $\mu$m to 50 $\mu$m) present in a first measuring space ZM1 shown in FIG. 4, and a magnification of 0.66 capable of observing large droplets (from 50 $\mu$m to 600 $\mu$m) present in a second measuring space ZM2, which makes it possible to obtain overall a measurement range from 10 $\mu$m to 600 $\mu$m. In addition, these magnifications make it possible to cover the entire diameter range without distortion in the overlap region.

In said preferred embodiment, the device 1 comprises a single camera 3 and the image acquisition means M2 in addition comprise, as shown in FIGS. 1 and 5:

a return prism 14, of the standard type, placed in the optical path of a first beam 7A of said beams 7A, 7B; and a semireflecting plate 16, of the standard type, placed in the optical path of the second beam 7B, and in the return optical path of the first beam 7A, downstream of the return prism 14.

It will be noted that the wavelength, the size of the optics and the magnification make it possible to define the minimum size of the particles that can be measured. The diameter of the diffraction spot or Airy disk is related to the wavelength and to the diameter of the pupil. The magnification makes it possible to choose the number of pixels which are covered by the smallest particle that it is desired to observe. In order to observe particles of size greater than or less than the aforementioned measurement range, the optical characteristics, that is the wavelength, the diameter of the optics and/or the magnification, should therefore be altered.

The depth of field is yet further increased by using the known principle of shadowgraphy in order to determine the size from images acquired by the image acquisition means M2. To this end, suitable and standard algorithms are integrated into the processing unit 4.

In the preferred embodiment shown in FIGS. 3 to 5, the device 1 additionally comprises:

a measuring element 2 in the form of a rod, which is provided close to its free end 2A with a through opening 19 containing the measuring region ZM which comprises the two aforementioned measuring spaces ZM1 and ZM2. The particles to be measured pass through the opening 19 in a flow direction E;

two pairs of windows 20A, 20B and 21A, 21B protecting the optical elements of the device 1 with respect to said flow of particles;

two return prisms 22 and 23 to return the light beams 7A and 7B to the measuring spaces ZM2 and ZM1, respectively;

a system 24 for blowing filtered air, partially shown in FIG. 3, for example controlled manually by means of a button 25 and preferably comprising a plurality of injectors (not shown) for blowing air over the external faces of the windows 20A, 20B, 21A and 21B, as illustrated by arrows f, so as to prevent any deposition of dirt (capable of causing optical perturbance) on these windows. In addition, the blowing system 24 makes it possible to deice the windows 20A, 20B, 21A and 21B if necessary. The blown air therefore has a temperature high enough to remove any ice from said windows;

an interference filter (not shown) which is fitted to the entrance of the camera 3 and which makes it possible to remove unwanted light capable of reaching said camera 3; and a control button 26 controlling the illumination means M1 and the image acquisition means M2, as illustrated by means of links 27 and 28, respectively.

In addition, all the optics of the device 1 are, preferably, subjected to an antireflection treatment in order to prevent interference.

Figure 6:
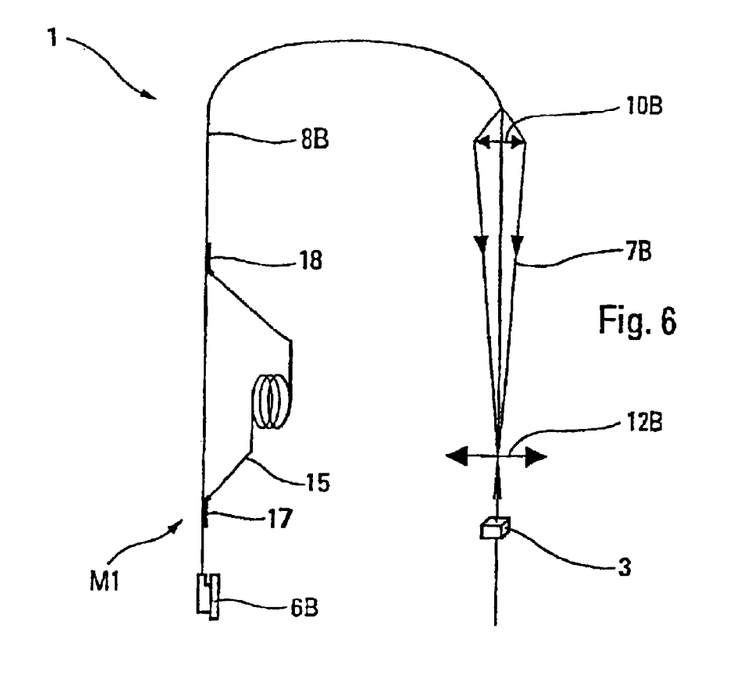
FIG. 6 illustrates schematically a particular embodiment of the invention.

Moreover, in a particular embodiment, shown partially and schematically in FIG. 6:

said illumination means M1 are constituted so as to emit two light flashes 7B spaced apart by a predetermined duration; said camera 3 is constituted so as to acquire an image on emission of each of said two light flashes 7B; and said processing unit 4 is constituted so as to determine the velocity vector of the particles, from the two images relating to said two light flashes 7B and from said predetermined duration.

The illumination means M1 comprise a single light source 6B and an optical fiber 8B which is connected to said light source 6B, in order to emit two light flashes 7B spaced apart by a predetermined duration. A delay line 15, comprising an optical fiber, preferably coiled, may be assembled in parallel to said optical fiber 8B, via optical couplers 17, 18.

When the laser source 6B emits a light pulse, the first half of the latter, corresponding to a first light flash, is sent directly to the camera 3 by means of the optical fiber 8B and the other half, which corresponds to the second light flash, enters, at the coupler 17, the delay line 15 which has, for example, a length of 200 meters, and is then sent to the camera 3 via the coupler 18 and the optical fiber 8B, with a delay corresponding to the time taken to pass through the delay line 15.

The velocity vector of the particles measured in this way can be used to calibrate the device 1 so as to obtain a representation of the flow in the measuring region ZM with respect to the flow in the environment in which the rod 2 is placed. The delay line 15 makes it possible to calibrate the device thereby giving an indication of the velocity vector of the particles. This indication makes it possible to determine whether the rod 2 is properly positioned with respect to the flow of the environment in which it is immersed. Once the correct position is identified and any risk of turbulent flow, which may be detrimental to the quality of the measurement, is prevented, the delay line is removed.

Figure 7:
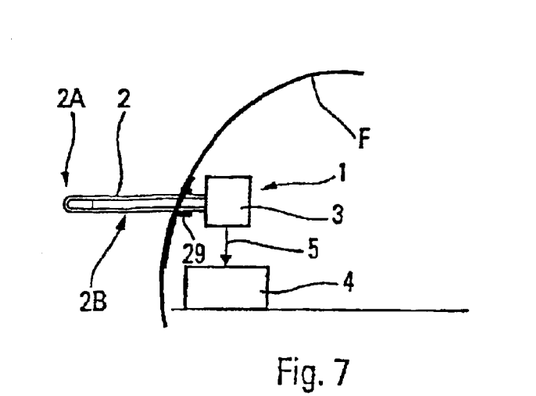
FIGS. 7 and 8 partially show a fuselage of an aircraft intended to accommodate a device according to the invention, in the presence and in the absence, respectively, of such a device.
Figure 8:
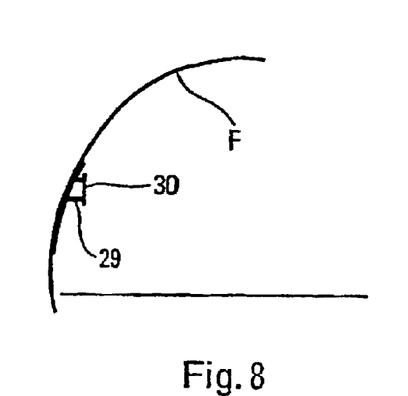

Moreover, in a preferred application, the device 1 according to the invention is assembled on an aircraft, for example a civil transport airplane, only part of the fuselage F of which is shown in FIGS. 7 and 8, in order to detect the size of water droplets present outside the aircraft so as to be able to characterize icing conditions and, if necessary, warn the pilot or pilots of the aircraft of the need to activate a deicing system.

In this case, the fuselage F of the aircraft is provided with a sleeve 29:

which is fitted in said fuselage F of the aircraft so as to create a through opening;

which has a diameter adapted to the diameter of the rod 2 of the device 1 such that the latter can be fitted in a sealed manner in said sleeve 29 (FIG. 7); and which is capable of being closed in a sealed manner, by means of a suitable and standard plug 30, in the absence of said rod 2 (FIG. 8).

Consequently, the device 1 according to the invention may be assembled and dismantled, easily and quickly. In addition, the aerodynamics of the aircraft are altered as little as possible.

Furthermore, with the exception of the part 2B (comprising at least the end 2A) of the rod 2 which is outside the fuselage F, all the rest of the device 1 is protected from the external environment and, in particular, from said particles, by said fuselage F.

In addition, said part 2B of the rod 2 is electrically insulated so as to make the device 1 unattractive to lightning. Consequently, the device 1 according to the invention makes it possible, in the aforementioned application, especially to:

measure the size of water droplets present in clouds;

measure the concentration of droplets, that is to say count their number per unit volume. This requires an accurate knowledge of the volume of the measuring spaces ZM1, ZM2;

provide the pilot with real time data required to carry out in-flight tests;

record all the information on board the aircraft. To this end, the processing unit 4 comprises or is combined with at least one storage unit (not shown); differentiate between water droplets and crystals; and measure the velocity (in a plane) of said water droplets.

A preferred application of the device 1 according to the invention therefore relates to the prevention and anticipation of icing conditions on an aircraft.

However, numerous other applications can also be envisaged, such as providing certification authorities with reliable quality information on the conditions encountered by an aircraft during in-flight tests, the certification of helicopters during stationary flights, the verification of conditions produced in icing wind tunnels, measurements on the ground during poor conditions of visibility (fog, etc.), etc.

What is claimed is:

1. A device for determining values of at least one parameter of particles, said device comprising:

a measuring element comprising a measuring region to accommodate said particles;

illumination means for illuminating said measuring region;

image acquisition means, comprising at least one camera, for acquiring at least one image of said measuring region illuminated by said illumination means; and processing means for determining the values of said parameter, from said image acquired by the camera, wherein said illumination means produce a point illumination source using a light beam having light rays focused onto an objective optic of the image acquisition means, said illumination means comprising at least one optical assembly including:

a light source that generates the light beam;

an optical fiber, connected at a first end to said light source, that transmits the light beam generated by said light source; and a field optic, fitted to a second end opposite said first end of said optical fiber, that focuses the light beam emerging from said optical fiber on the center of the objective optic of the acquisition means.

2. The device as claimed in claim 1, wherein said optical fiber is a monomode fiber.

3. The device as claimed in claim 1, wherein said light source generates a coherent light beam.

4. A device for determining values of at least one parameter of particles, said device comprising:

a measuring element comprising a measuring region to accommodate said particles;

illumination means for illuminating said measuring region;

image acquisition means, comprising at least one camera, for acquiring at least one image of said measuring region illuminated by said illumination means; and processing means for determining the values of said parameter, from said image acquired by the camera, wherein:

said illumination means produce a point illumination source using a light beam having light rays focused onto an objective optic of the image acquisition means, said camera comprises means for opening the camera in order to acquire the image, said illumination means produce illumination in the form of light flashes, and said illumination means emit at least two light flashes during one and the same opening of the camera on acquiring the image.

5. The device as claimed in claim 4, wherein said illumination means comprise at least one pulsed laser with a saturable absorber, in order to emit said light flashes.

6. A device for determining values of at least one parameter of particles, said device comprising:

a measuring element comprising a measuring region to accommodate said particles;

illumination means for illuminating said measuring region;

image acquisition means, comprising at least one camera, for acquiring at least one image of said measuring region illuminated by said illumination means; and processing means for determining the values of said parameter, from said image acquired by the camera, wherein:

said illumination means produce a point illumination source using a light beam having light rays focused onto an objective optic of the image acquisition means, and said illumination means emit in a sequential manner at least two light beams having different diameters.

7. The device as claimed in claim 6, wherein:

said illumination means comprise two laser sources associated with optics, respectively, of different magnifications, and said image acquisition means comprise a single camera and optical means for directing the two laser beams emitted by said two laser sources onto said camera.

8. The device as claimed in claim 1, wherein said processing means determine said parameter by shadowgraphy.

9. A device for determining values of at least one parameter of particles, said device comprising:

a measuring element comprising a measuring region to accommodate said particles;

illumination means for illuminating said measuring region;

image acquisition means, comprising at least one camera, for acquiring at least one image of said measuring region illuminated by said illumination means; and processing means for determining the values of said parameter, from said image acquired by the camera, wherein:

said illumination means produce a point illumination source using a light beam having light rays focused onto an objective optic of the image acquisition means, said illumination means emit two light flashes spaced apart by a predetermined duration, said camera acquires an image on emission of each of said two light flashes, and said processing means determine, as the parameter, the velocity vector of said particles, from the two images relating to said two light flashes and from said predetermined duration.

10. The device as claimed in claim 9, wherein an optical fiber is connected to said light source.

11. The device as claimed in claim 1, further comprising an interference filter which is fitted to the entrance of said camera.

12. The device as claimed in claim 1, wherein the objective and field optics have an applied antireflection treatment.

13. The device as claimed in claim 1, wherein said measuring region is delimited by at least one window.

14. The device as claimed in claim 13, further comprising means for blowing air over the external face of said window.

15. The device as claimed in claim 1, wherein said measuring element is a rod provided with a through opening at a first of its ends, said through opening containing said measuring region.

16. The device as claimed in claim 15, further comprising a protection which protects the entire said device, except for at least said first end of the rod which is placed in an environment containing said particles, against said particles.

17. The device as claimed in claim 15, wherein at least said first end of the rod is electrically insulated.

18. An aircraft, comprising the device specified in claim 1, wherein the device determines the values of said parameter of water droplets present outside said aircraft.

19. An aircraft comprising the device in claim 15 and further comprising a sleeve:

which is fitted into a fuselage of the aircraft so as to create a through opening;

which has a diameter adapted to the diameter of said rod such that the rod can be fitted in a sealed manner in said sleeve; and which may be closed in a sealed manner, in the absence of said rod.

* * * * *